United States Patent
Lamb et al.

(10) Patent No.: US 7,173,063 B1
(45) Date of Patent: Feb. 6, 2007

(54) TOPOISOMERASE POISONS FOR THE TREATMENT OF PROLIFERATIVE DISORDERS

(75) Inventors: John R. Lamb, Shoreline, WA (US); Julian Simon, Seattle, WA (US); Heather Dunstan, San Diego, CA (US); Stephen H. Friend, Bryn Mawr, PA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 10/129,936

(22) PCT Filed: Nov. 10, 2000

(86) PCT No.: PCT/US00/30804

§ 371 (c)(1),
(2), (4) Date: Jan. 13, 2003

(87) PCT Pub. No.: WO01/34151

PCT Pub. Date: May 17, 2001

(51) Int. Cl.
*A61K 31/16* (2006.01)
*A61K 31/165* (2006.01)
*C07C 241/00* (2006.01)
*C07C 233/00* (2006.01)

(52) U.S. Cl. .................. 514/615; 514/613; 514/614; 514/616; 514/617; 564/123; 564/148; 564/150; 564/153

(58) Field of Classification Search ........ 514/613–617; 564/123, 153, 148, 150
See application file for complete search history.

(56) References Cited

U.S. PATENT DOCUMENTS 5,395,934 A    3/1995   Matyus et al.

FOREIGN PATENT DOCUMENTS

| EP | 0 665 223 A1 | 8/1995 |
| WO | WO 98/40102 * | 9/1998 |
| WO | WO 98/40102 A1 | 9/1998 |

OTHER PUBLICATIONS

Parmar et al. 'Synthesis of substituted benzylidinohydrazines and their monoamine oxidase inhibitory and Anticonvulsant properties,' Journal of Pharmaceutical Sciences, 1975, Vo. 64, No. 1, pp. 154-157.*

(Continued)

*Primary Examiner*—Shengjun Wang
(74) *Attorney, Agent, or Firm*—Townsend and Townsend and Crew LLP

(57) ABSTRACT

Methods for the treatment of a proliferative disorder are provided in which a subject in need of such treatment is administered an effective amount of a compound selected from: compounds of formula (I) or a pharmaceutically acceptable salt thereof, wherein $X^1$ and $X^2$ are independently H, Cl, F, Br, I, CN, $CF_3$ or $NO_2$, and $Ar^1$ is a substituted or unsubstituted aryl or a substituted or unsubstituted heteroaryl; and compounds of formula (II) wherein $X^3$ and $X^4$ are each independently H, Cl, F, Br, I, CN, $CF_3$ or $NO_2$; Y is $(C_2-C_6)$alkylene or $(C_2-C_6)$heteroalkylene; and Z is Cl, F, Br, I, CN, $CF_3$ or $NO_2$.

5 Claims, 9 Drawing Sheets

OTHER PUBLICATIONS

Sinha 'Topoisomerase inhibitors,' Drugs, 1995, Vo. 49, No. 1, pp. 11-19.*

Dancey et al. 'Current perspective on camptothecins in cancer treatment,' British Journal of Cancer, 1996, vol. 74, pp. 327-338.*

Kim, J. et al., "Alkylation of 4,5-Dichloropyridazan-6-one with α,ω-dibromoalkanes or 4,5-dichloro-1-(ω-bromoalkyl)pyridazin-6-ones" Heterocyclic Chem. 34(1):209-214 (1997).

Parmar, S. et al., "Synthesis of substituted benzylidinohydrazines and their monoamine oxidase inhibitory and anticonvulsant properties" Journal of Pharmaceutical Sciences 64 (1):154-157 (1975).

Santagati, N. et al., "Synthesis and pharmacological study of a series of 3(2H)-pyridazinones as analgesic and anti-inflammatory agents" Ed. Sci. 40 (12):921-929 (1985).

* cited by examiner

Compound Ia

Compound IIa

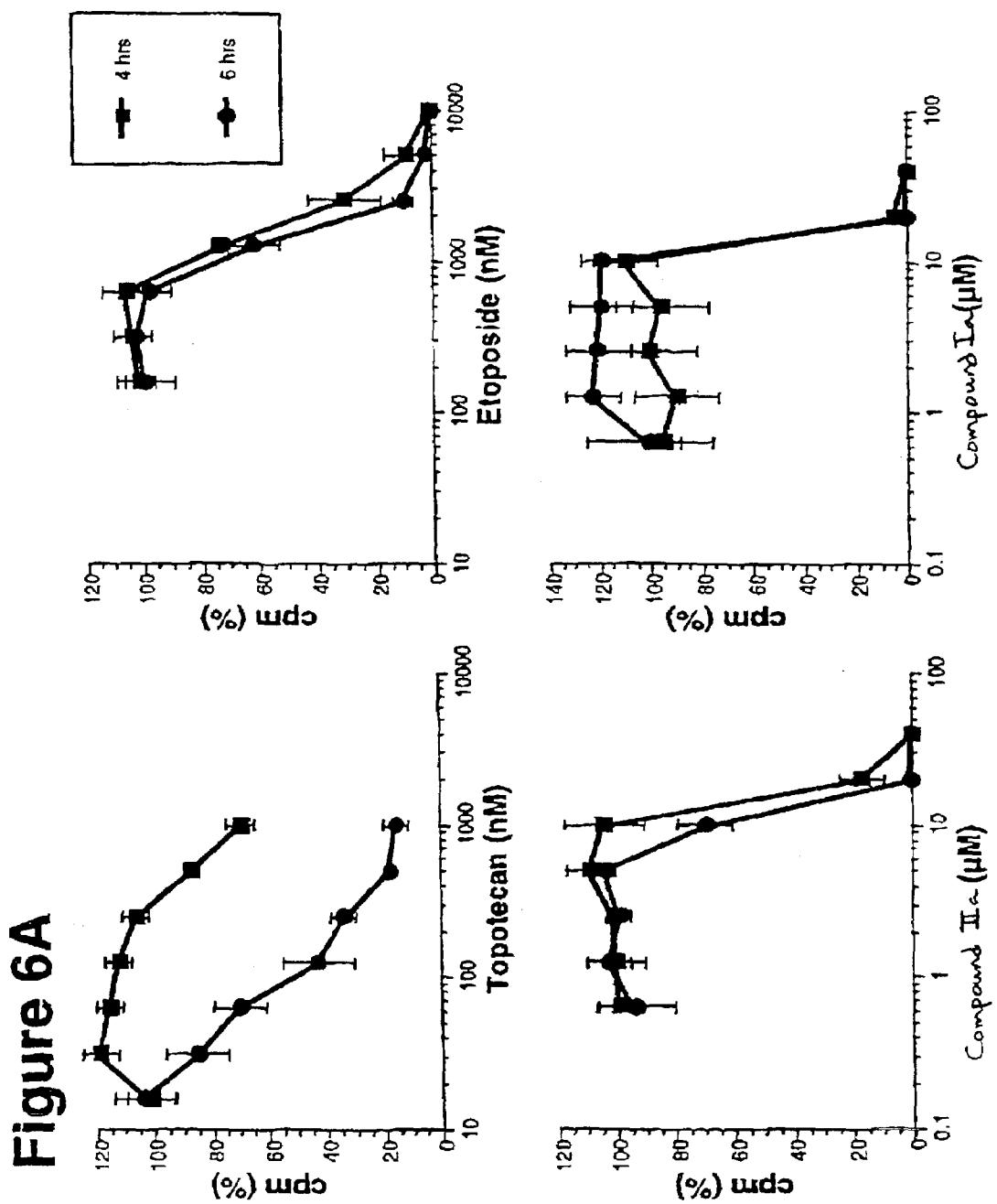

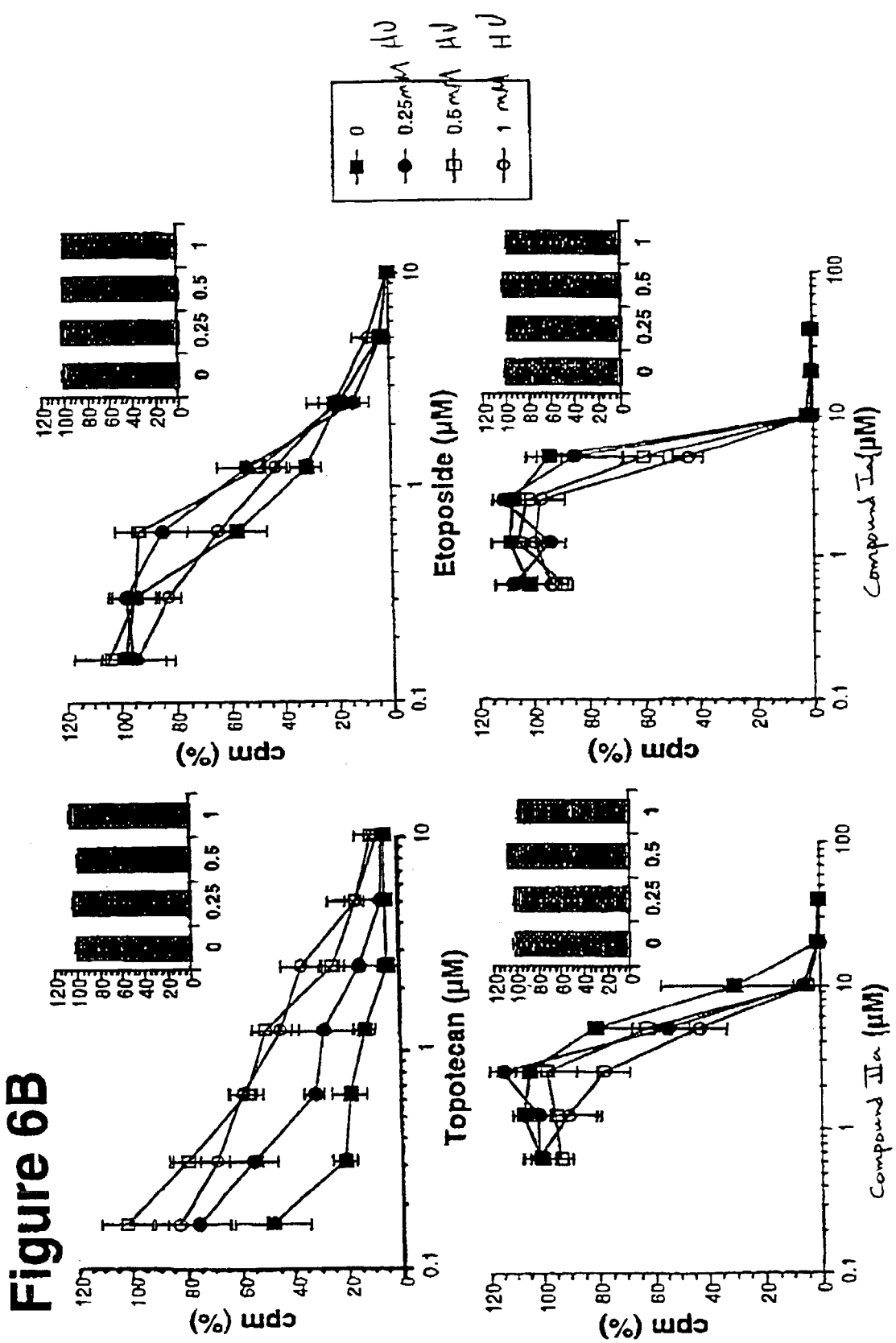

TOPOISOMERASE POISONS FOR THE TREATMENT OF PROLIFERATIVE DISORDERS

STATEMENT AS TO RIGHTS TO INVENTIONS MADE UNDER FEDERALLY SPONSORED RESEARCH AND DEVELOPMENT

A portion of the work described herein was carried out under contract with the National Cancer Institute (N01BC65017). Accordingly, the U.S. Government may have certain rights in this invention.

BACKGROUND OF THE INVENTION

The DNA topoisomerases are a family of enzymes that play multiple roles in the maintenance and propagation of the genomes of both prokaryotes and eukaryotes. Compounds that act as effective cellular inhibitors or "poisons" of topoisomerases act as cytotoxic agents through induction of DNA damage.

Topoisomerases have been reviewed in, for example, Wigley, D. B. (1995) *Ann. Rev. Biophys. Biomolec. Struct.* 24: 185–208. Type I DNA topoisomerases (EC 5.99.1.2; also known as relaxing enzyme, untwisting enzyme, swivelase, nicking-closing enzyme, and omega-protein) can convert one topological isomer of DNA into another. In particular, these topoisomerases can relax superhelical turns in DNA, interconvert simple and knotted rings of single-stranded DNA, and intertwist single-stranded rings of complementary sequences. Additionally, the type I topoisomerases act by catalyzing the transient breakage of DNA, one strand at a time, and the subsequent rejoining of the strands. In the process of breaking the strand, a type I topoisomerase (or topoisomerase I or topo I) simultaneously forms a topoisomerase-DNA link in which the hydroxyl group of a tyrosine residue is joined to a 5'-phosphate on DNA, at one end of the enzyme-severed DNA strand.

Similarly, type II DNA topoisomerases (EC 5.99.1.3; also known as DNA topoisomerase II and DNA gyrase) can change the topology of double-stranded DNA molecules, causing, for example, the relaxation of supercoiled DNA molecules, catenation, decatenation, knotting and unknotting of circular DNA (for a review, see Watt and Hickson (1994) *Biochem. J.* 303: 681–695). Type II topoisomerases act by a concerted breakage and reunion activity involving both strands of the DNA duplex. This activity is absolutely required for DNA replication and transcription.

Still other types of topoisomerases have been identified, including a cDNA encoding human DNA topoisomerase III (Hanai, et al. *Proc. Nat. Acad. Sci.* 93: 3653–3657 (1996)) which is commonly deleted in patients with the Smith-Magenis syndrome (Elsea, et al., *Am. J. Med. Genet.* 75: 104–108 (1998)). DNA topoisomerase III protein is homologous to the *E. coli* DNA topoisomerase I subfamily of enzymes, but shares no significant sequence homology with eukaryotic DNA topoisomerase I. Topoisomerase III catalyzes the reduction of supercoils in highly negatively supercoiled DNA.

Currently, topoisomerase inhibitors are classified into two general types. The class designated as "poisons" have in common the property of causing "trapping" of the target topoisomerase in the form of a covalent complex with the nucleic acid substrate. The "non-poison" class inhibits the enzymatic activity of the topoisomerase without specific effects on steps of the catalytic cycle that involve formation or resolution of the enzyme-DNA covalent intermediate. Of the DNA topoisomerase inhibitors currently used as clinical antibiotic or antineoplastic agents, the "poisons" seem to be most effective, probably because such compounds result in the accumulation of irreversible genotoxic damage in target cells.

Additionally, there are currently two type I topoisomerase ("Topo I") poisons approved for the treatment of cancer in the United States—topotecan and irinotecan (Abang, et al., *Seminars in Hematology* 35: 13–21 (1998), Arbuck, et al., *Seminars in Hematology* 35: 3–12 (1998), Thompson, et al., *Biochimica et Biophysica Acta.* 1400: 301–19 (1998)), both of which are derivatives of camptothecin. These two agents have demonstrated clinical activity, but in rather distinct tissue settings (Abang, et al., *Seminars in Hematology* 35: 13–21 (1998), Arbuck, et al., *Seminars in Hematology* 35: 3–12 (1998), Thompson, et al., *Biochimica et Biophysica Acta.* 1400: 301–19 (1998)). The use of these FDA-approved Topo I poisons is further restricted by tumor resistance and dose limiting toxicities (Abang, et al., *Seminars in Hematology* 35: 13–21 (1998) Arbuck, et al., *Seminars in Hematology* 35: 3–12 (1998), Cersosimo, et al., *The Annals of Pharmacotherapy* 32: 1334–43 (1998), Dingemans, et al., *Biochimica et Biophysica Acta.* 1400: 275–88 (1998), Kollmannsberger, et al., *Oncology,* 56: 1–12 (1999), Larsen, et al., *Biochimica et Biophysica Acta.* 1400: 257–74 (1998), Slichenmyer, et al., *Chemotherapy & Pharmacology* 34 Suppl: S53–7 (1994)). Significant interest has now developed in identifying additional compounds that target Topo I and that may overcome some of these limitations. This has resulted in the description of a number of Topo I-targeted agents including camptothecin derivatives (Pommier, et al., *Biochimie* 80: 255–270 (1998)), molecules that bind DNA by intercalation (Fukasawa, et al., *International Journal of Cancer* 75: 145–50 (1998), Gatto, et al., *Cancer Research* 56: 2795–800 (1996), Guano, et al., *Molecular Pharmacology* 56: 77–84 (1999), Pilch, et al., *Biochemistry* 36: 12542–53 (1997). Yoshinari, et al., *Cancer Research* 55: 1310–5 (1995)) or that bind to the minor groove in DNA (Pilch, et al., *Biochemistry* 36: 12542–53 (1997), Bridewell, et al., *Oncology Research* 9: 535–42 (1997), Chen, et al., *Academy of Sciences of the United States of America* 90: 8131–5 (1993), Chen, et al., *Cancer Research* 53: 1332–7 (1993), Martinez, et al., *National Academy of Sciences of the United States of America* 96: 3496–501 (1999), Nitiss, et al., *Cancer Research* 57: 4564–9 (1997), Sim, et al., *Biochemistry* 36: 13285–91 (1997), Takebayashi, et al., *Proceedings of the National Academy of Sciences of the United States of America* 96: 7196–201 (1999), Xu, et al., *Biochemistry* 37: 3558–66 (1998)), and others (Kohlhagen, et al, *Molecular Pharmacology* 54: 50–8 (1998)). Additionally, compounds that are less selective and act as both Topo I and Topo II poisons (Leteurtre, et al., *Journal of Biological Chemistry* 269: 28702–7 (1994), Poddevin, et al., *Molecular Pharmacology* 44: 767–74 (1993), Riou, et al., *Cancer Research* 53: 5987–93 (1993), Yamashita, et al., *Biochemistry* 30: 5838–45 (1991)) have been described.

Camptothecin has been shown to act by stabilizing an otherwise transient reaction intermediate between Topo I and DNA (Abang, et al., *Seminars in Hematology* 35: 13–21 (1998), Arbuck, et al., *Seminars in Hematology* 35: 3–12 (1998). Pommier, et al., *Biochimie* 80: 255–270 (1998)). In these trapped complexes Topo I is covalently attached to the 3' end of a single strand break. Removal of camptothecin results in rapid religation of the break by Topo I and averts toxicity. Toxicity occurs during S-phase when a replication fork encounters a trapped complex and converts it into a double strand break (DSB, D'Arpa, et al., *Cancer Research*

50: 6919–24 (1990), Hsiang, et al., *Cancer Research* 49: 5077–82 (1989), Holm, et al., *Cancer Research* 49: 6365–8 (1989)). Consequently, the toxicity of camptothecin and its derivatives show a strong dependency on the time of exposure in vitro (Cheng, et al., *Oncology Research* 6: 269–79 (1994)) and in vivo (Haas, et al., *Cancer Research* 54: 1220–6 (1994), Houghton, et al., *Cancer Chemotherapy & Pharmacology* 36: 393–403 (1995), Rodman, et al., *Journal of Clinical Oncology* 5: 1007–14 (1987)). Furthermore, in tissue culture cell lines camptothecin toxicity can be inhibited by co-treatment with DNA synthesis inhibitors (D'Arpa, et al., *Cancer Research* 50: 6919–24 (1990), Hsiang, et al., *Cancer Research* 49: 5077–82 (1989), Holm, et al., *Cancer Research* 49: 6365–8 (1989)). In cancer cells, camptothecin resistance can arise from a prolonged ability to arrest in G2 (Goldwasser, et al., *Cancer Research* 56: 4430–7 (1996), Dubrez, et al., *Leukemia* 9: 1013–24 (1995)), and from downregulation or mutation of Topo I (Arbuck, et al., *Seminars in Hematology* 35: 3–12 (1998), Larsen, et al., *Biochimica et Biophysica Acta*. 1400: 257–74 (1998)).

The clinical activity of the topoisomerase I poisons has been their ability to induce double-stranded breaks in the genome of dividing cells. Such poisons have been used to treat proliferative diseases such as cancer. However, currently available topoisomerase I poisons, such as camptothecin, are toxic only during S-phase of the cell cycle. What is needed in the art are new methods for inducing double-stranded breaks in DNA in all phases of the cell cycle by irreversibly trapping topoisomerase I-DNA complexes. Surprisingly, the present invention provides such methods and identifies compounds that are useful in such methods.

SUMMARY OF THE INVENTION

In one aspect, the present invention provides methods for the treatment of proliferative disorders, the method comprising administering to a subject in need of such treatment an effective amount of a compound selected from the compounds of formula I,

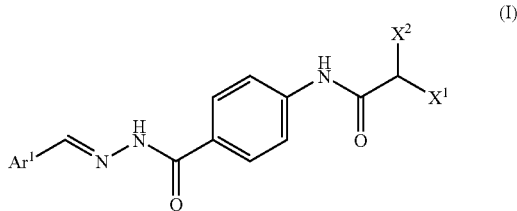

(I)

or a pharmaceutically acceptable salt thereof, wherein $X^1$ and $X^2$ are independently H, Cl, F, Br, I, CN, $CF_3$ or $NO_2$, and $Ar^1$ is a substituted or unsubstituted aryl or a substituted or unsubstituted heteroaryl; and compounds of formula II,

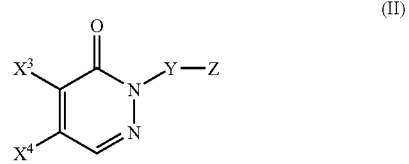

(II)

wherein $X^3$ and $X^4$ are each independently H, Cl, F, Br, I, CN, $CF_3$ or $NO_2$; Y is $(C_2-C_6)$alkylene or $(C_2-C_6)$heteroalkylene; and Z is Cl, F, Br, I, CN, $CF_3$ or $NO_2$.

In another aspect, the present invention provides methods for selectively inducing DNA double-strand breaks without inducing DNA damage that is subject to nucleotide excision repair or daughter strand gap repair in a cell, by contacting the cell with an effective amount of a compound identified above.

In still another aspect, the present invention provides certain novel compounds of formula I or of formula II, and pharmaceutical compositions containing at least one of those compounds.

BRIEF DESCRIPTION OF THE DRAWINGS

FIG. 2 illustrates the toxicity of various compounds to yeast strains with altered levels of topo I or II.

FIG. 4 shows the toxicity in repair-deficient vertebrate cells and human tumor cell lines. Toxicity was measured using the thymidine incorporation assay described in the Example.

FIG. 6 illustrates the effect of exposure time and hydroxyurea on the toxicity of compound Ia and compound IIa. FIG. 6A shows the effect of exposure time on the toxicity of topotecan (Topo I poison), etoposide (Topo II poison), compound Ia and compound IIa (both Topo I poisons). Rat1a fibroblasts were exposed to compound during growth for either four or six hours, the media was changed, then cells were grown for an appropriate period such that total incubation time was 96 hours, and processed as described in the Example below. FIG. 6B shows the effect of co-treatment with the DNA synthesis inhibitor hydroxyurea (HU). Rat1a fibroblasts were exposed to various concentrations of topotecan, etoposide, compound Ia or compound IIa in combination with 0, 0.25, 0.5 or 1 mM HU for six hours, then processed as described in the Example below. The bar graph insets for each graph show growth inhibition by HU alone.

DESCRIPTION OF THE SPECIFIC EMBODIMENTS

Figure 1:
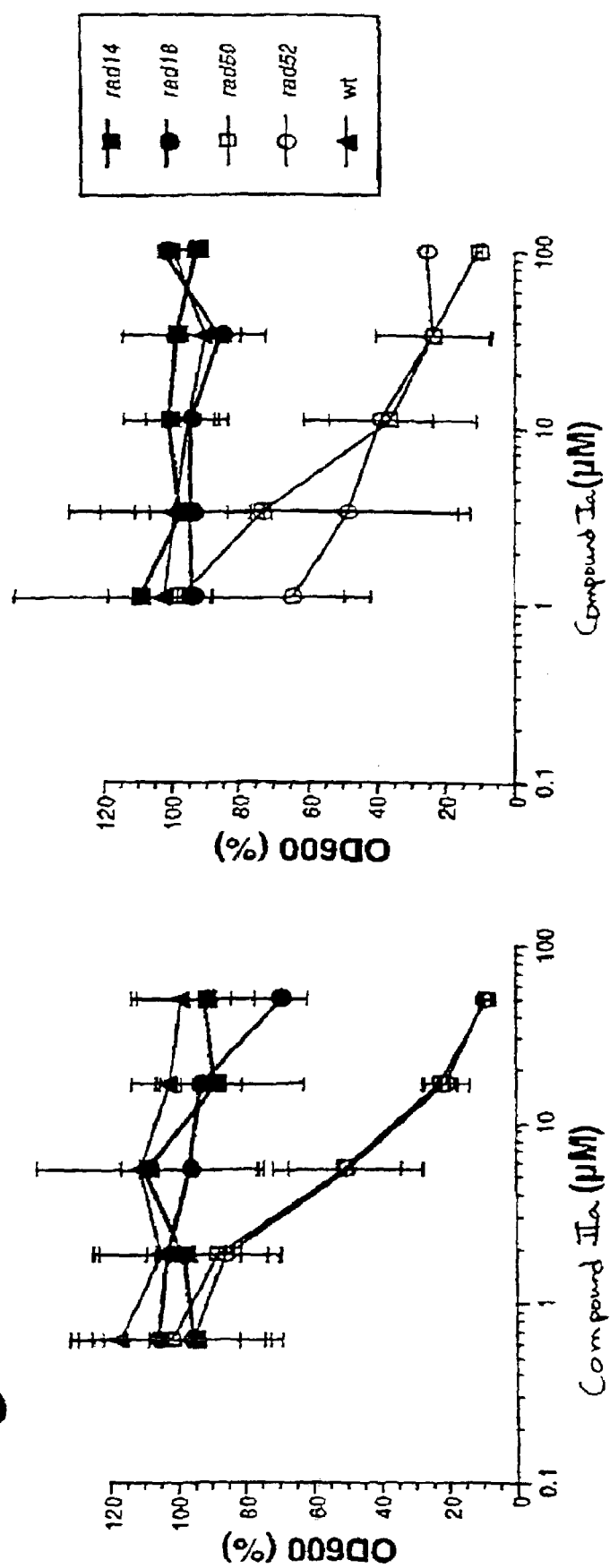
FIG. 1 illustrates the toxicity of compounds I and II in DNA repair-deficient yeast. Relative growth was measured as described in the Example below. The yeast strains are identified as (i) repair proficient (wt); (ii) deficient in nucleotide excision repair (rad14); (iii) deficient in daughter strand gap repair (rad18); and (iv) deficient in double strand break repair (rad50 and rad52).

Abbreviations and Definitions:

The abbreviations used herein have their conventional meaning within the chemical and biological arts. For example: CFU, colony forming units; HU, hydroxy urea; DSB, double strand break; NHEJ, non-homologous end joining; Topo I, topoisomerase I or type 1 topoisomerase; SDS, sodium dodecyl sulfate; $Et_3N$: triethylamine; MeOH: methanol; and DMSO: dimethylsulfoxide.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkylene" by itself or as part of another substituent means a divalent radical derived from an alkane, as exemplified by —$CH_2CH_2CH_2CH_2$—.

The term "acyl" is used in its conventional sense and refers to a radical typically having from two to twelve carbon atoms and derived from a carboxylic acid by removal of the —OH group. For example, acyl is meant to include acetyl, propionyl, pivaloyl, pentanoyl and the like. Typically, the acyl group will be unsubstituteted, but may have substituents selected from the group provided below for alkyl where those groups are compatible with the carbonyl functionality of the acyl group.

The terms "alkylamino" and "dialkylamino" are used in their conventional sense, and refer to those alkyl groups attached to the remainder of the molecule via a nitrogen atom.

The term "heteroalkylene" refers to a divalent radical derived from alkylene by replacement of a carbon atom with a heteroatom. Examples include —$CH_2CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$–$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Each of the above terms (e.g. "alkyl," "aryl" and "heteroaryl") are meant to include both substituted and unsubstituted forms of the indicated radical. Preferred substituents for each type of radical are provided below.

Substituents for the alkyl radicals (including those groups often referred to as alkylene) can be a variety of groups selected from: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2m'+1), where m' is the total number of carbon atoms in such radical. R', R" and R'" each independently refer to hydrogen, unsubstituted ($C_1$–$C_8$)alkyl or heteroalkyl (an alkyl group in which one carbon has been replaced by a heteroatom), unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$).

Similarly, substituents for the aryl and heteroaryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R'", —NH—C($NH_2$)=NH, —NR'C($NH_2$)=NH, —NH—C($NH_2$)=NR', —S(O)R', —S(O)$_2$R', —S(O)$_2$NR'R", —$N_3$, —CH(Ph)$_2$, perfluoro ($C_1$–$C_4$)alkoxy, and perfluoro($C_1$–$C_4$)alkyl, in a number ranging from zero to the total number of open valences on the aromatic ring system; and where R', R" and R'" are independently selected from hydrogen, ($C_1$–$C_8$)alkyl and heteroalkyl, unsubstituted aryl and heteroaryl, (unsubstituted aryl)-($C_1$–$C_4$)alkyl, and (unsubstituted aryl)oxy-($C_1$–$C_4$)alkyl.

Two of the substituents on adjacent atoms of the aryl or heteroaryl ring may optionally be replaced with a substituent of the formula —T—C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula —A—(CH$_2$)$_r$—B—, wherein A and B are independently —CH$_2$—, —O—, —NH—, —S—, —S(O)$_2$—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$–C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example. Berge, S. M., et al, "Pharmaceutical Salts". *Journal of Pharmaceutical Science,* 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the compounds used herein can be in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

Two new classes of topoisomerase I poisons have now been identified using cell based assays. These two classes of compounds are structurally unrelated to camptothecin or any other described Topo I poison. The compounds are toxic in human tumor and vertebrate cell lines. Additionally, their toxicity is wholly dependent on Topo I in yeast and that at least one class can interact with human Topo I and a camptothecin resistant mutant of yeast Topo I. Like camptothecin, these two classes of compounds produce damage which can be repaired by the homologous recombination pathway of DSB repair (at least in yeast, where this pathway predominates), but not by non-homologous end rejoining. The toxicity of these compounds, in contrast to that of camptothecin, does not show a strong dependence on the length of exposure and is not inhibited by hydroxyurea, indicating significant mechanistic differences. Accordingly, the classes of compounds provided herein will find particular utility in the treatment of proliferative disorders such as cancer (including colorectal cancer, ovarian cancer, small cell lung carcinoma) and other proliferative disorders.

Proliferative disorders as used herein are disorders wherein cells present in the subject having the disorder proliferate at an abnormally high rate relative to wild-type cells and wherein the abnormal proliferation is a cause of the disorder. Proliferative disorders include, but are not limited to, cancer, hyperplasia, autoimmune disease, and certain viral diseases. Proliferative disorders such as cancer include, but are not limited to colorectal carcinoma, ovarian cancer, small cell lung cancer, and non-Hodgkin's lymphoma. Autoimmune diseases include, but are not limited to, rheumatoid arthritis, lupus erythematosus, and scleroderma. Viral diseases include, but are not limited to retroviral infections such as HIV.

Description of the Embodiments

In one aspect, the present invention provides methods for the treatment of a proliferative disorder, comprising administering to a subject in need of such treatment an effective amount of a compound of formula I or a compound of formula II.

In one group of embodiments the compounds used are those of formula I,

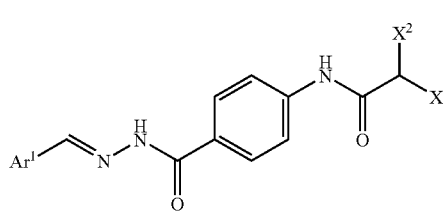
(I)

wherein $X^1$ and $X^2$ are independently H, Cl, F, Br, I, CN, $CF_3$ or $NO_2$, and $Ar^1$ is a substituted or unsubstituted aryl or a substituted or unsubstituted heteroaryl.

Preferably, for the compounds of formula I, $X^1$ is H or Cl and $X^2$ is F or Cl. More preferably, $X^1$ is H and $X^2$ is Cl.

Turning next to $Ar^1$, this aryl group is preferably a mono- or di-substituted phenyl group. In certain preferred embodiments, $Ar^1$ is a mono- or di-substituted phenyl group having substituents selected from F, Cl, Br, I, CN, $CF_3$, $OCF_3$ and $NO_2$. Still further preferred are those embodiments in which the substituents are in positions para to the phenyl group's point of attachment to the remainder of the molecule.

In a most preferred group of embodiments, $X^1$ is H, $X^2$ is Cl, and $Ar^1$ is 4-chlorophenyl or 4-nitrophenyl.

In another group of embodiments, the compounds used are those of formula II,

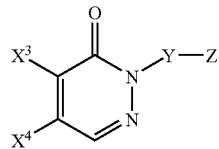
(II)

wherein $X^3$ and $X^4$ are each independently H, Cl, F, Br, I, CN, $CF_3$ or $NO_2$; Y is $(C_2-C_6)$alkylene or $(C_2-C_6)$heteroalkylene; and Z is Cl, F, Br, I, CN, $CF_3$ or $NO_2$.

In this latter group of embodiments, $X^3$ and $X^4$ are preferably independently F or Cl. More preferably, $X^3$ and $X^4$ are each Cl. Additionally, Y is preferably a $(C_2-C_4)$ alkylene group, optionally substituted with one or more fluorine atoms. More preferably, Y is an ethylene or propylene group. Other preferred embodiments are those in which Z is F, Cl or $CF_3$, more preferably Z is Cl.

In the most preferred embodiments, the present methods will use one or more compounds having the formula indicated below:

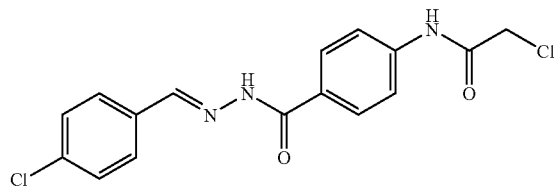
Ia

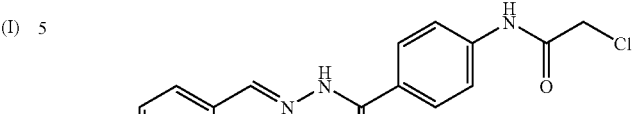
Ib

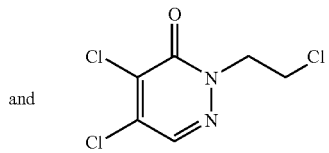
IIa and

A variety of proliferative disorders can be treated using the compounds described above. In particular, a variety of cancers can be treated. The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells. Additionally, the phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

In another aspect, the present invention provides methods for selectively inducing DNA double strand breaks in all phases of the cell cycle by the irreversible interaction with topoisomerase I, by contacting the cell with an effective amount of a compound identified above.

In yet another aspect, the present invention provides novel compounds within the general formula I and II above, as well as pharmaceutical compositions containing those compounds.

Preparation of Compounds

Compounds of formula I can be prepared from readily available starting materials, using methods such as those described in Singh, et al., *Arch. Pharm.* 317:609–614 (1984). Scheme 1 illustrates a general synthesis for the compounds of formula I.

SCHEME 1

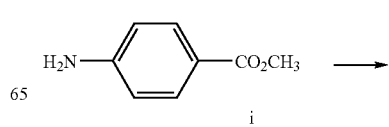
i

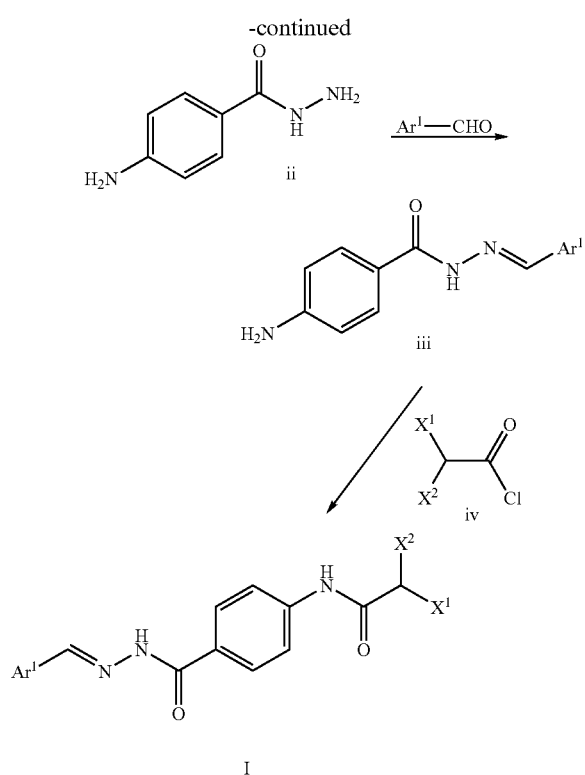

As can be seen in Scheme 1, an aryl methyl ester (i) can be converted to an aromatic acid hydrazide (ii), typically upon treatment with hydrazine. Treatment of ii with an aromatic aldehyde ($Ar^1$—CHO) in the presence of, for example, glacial acetic acid produces the corresponding hydrazone (iii). Conversion of iii to compounds of formula I involves acylation of the amino group in iii with a substituted acetyl chloride (iv) in the presence of a suitable base (e.g., triethylamine or another non-nucleophilic base).

Similarly, compounds of formula II can be prepared in a manner similar to that described in U.S. Pat. No. 4,978,665.

Formulation of Compounds

For use in the present invention, the compounds noted above will typically be combined with other ingredients in a pharmaceutically acceptable formulation. By "pharmaceutically acceptable" it is meant the carrier, diluent or excipient must be compatible with the other ingredients of the formulation and not deleterious to the recipient thereof.

The pharmaceutical compositions used in the present methods may conveniently be presented in unit dosage form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions are also useful and contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water. Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Of course, the compounds provided above can be formulated in a variety of other formats well-known to those of skill in the art (see, Remington's Pharmaceutical Sciences, A. R. Genaro (ed), 19th ed., Mark Publishing Co., Easton, Pa. (1995))

The pharmaceutical composition and method of the present invention may further comprise other therapeutically active compounds as noted herein which are usually applied in the treatment of the above mentioned pathological conditions.

Administration of Compounds

As noted above, the present invention provides methods of treating proliferative disorders by administering to a subject having such a disease or condition, a therapeutically effective amount of a compound of formula I or II, above. The "subject" is defined herein to include animals such as mammals, including, but not limited to, primates (e.g., humans), cows, sheep, goats, horses, dogs, cats, rabbits, rats, mice and the like.

The term "therapeutically effective amount" or "effective amount" means the amount of the subject compound that will elicit the biological or medical response of a tissue, system, animal or human that is being sought by the researcher, veterinarian, medical doctor or other clinician.

Diseases and conditions associated with proliferation and/or cancer can be treated with the present compounds and compositions. In one group of embodiments, diseases or conditions include cancers, and diseases in which angiogenesis or neovascularization play a role (e.g., neoplastic diseases, retinopathy and macular degeneration). In another group of embodiments, the disease is a viral disease. In still another group of embodiments, the disease is an autoimmune disease.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require topoisomerase I poisoning, an appropriate dosage level will generally be about 0.001 to 100 mg per kg patient body weight per day which can be administered in single or multiple doses. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can also be combined with other compounds having related utilities to prevent and treat cancer or other proliferative disorders as noted above.

EXAMPLES

The example below demonstrates the activity and selectivity for a representative example of each of formula I and formula II. Briefly, assays were run to identify compounds that were selectively toxic to cells defective in double strand break repair, without being toxic to cells defective in either nucleotide excision repair or daughter strand gap repair.

Material and Methods.

Yeast Strain Constructions and Plasmids.

All yeast strains used in this work are listed in Table 1. The strains are derived from the A364a genetic background, with the exception of BY4705, which is derived from the S288C background. Gene disruptions were generated by PCR fragment directed replacement (Baudin, et al., *Nucleic Acids Research* 21: 3329–30 (1993), Guldener, et al., *Nucleic Acids Research* 24: 2519–24 (1996)). Yeast overexpressing topoisomerase II was constructed by a PCR fragment directed promoter replacement of the topoisomerase II promoter with the yeast GPD promoter flanked upstream by the URA3 marker. All strains (except BY4705) bear the pleitropic drug sensitizing mutations erg6, pdr1, and pdr3 (Balzi, et al., *Journal of Bioenergetics & Biomembranes* 27: 71–6 (1995), Delaveau, et al, *Molecular & General Genetics* 244: 501–11 (1994), Gaber, et al., *Molecular & Cellular Biology* 9: 3447–56 (1989), Saunders, et al., *Canadian Journal of Genetics & Cytology*, 24: 493–503 (1982). Subik, et al, *Current Genetics* 10: 665–70 (1986)). The haploid yeast strain BY4705 (Brachmann, et al., *Yeast* 14: 115–32 (1998)) was used in the experiments described in FIG. 5. Plasmids expressing yeast or human topoisomerase I genes under the GAL promoter (Knab, et al., *Journal of Biological Chemistry* 268: 22322–30 (1993). Knab, et al., *Journal of Biological Chemistry* 270: 6141–8 (1995)) were transformed into BY4705 using standard procedures.

TABLE 1

| | Relevant mutation(s) | Genotype |
|---|---|---|
| SPY50644 | none (wild-type control) | MATa erg6ΔLEU2 pdr1ΔLEU2 pdr3Δhis G::URA3::hisG ade2 ade3 leu2 ura3 cyh2 |
| SPY50891 | rad18 | MATa rad18ΔURA3 erg6ΔTRP1 pdr1ΔLEU2 pdr3ΔhisG ade2 ade3 leu2 trp1 ura3 cyh2 |
| SPY50740 | rad14 | MATa rad14Δkan$^r$ erg6ΔLEU2 pdr1ΔLEU2 pdr3ΔhisG::URA3::hisG ade2 ade3 leu2 ura3 cyh2 |
| SPY50652 | rad50 | MATa rad50Δkan$^r$ erg6ΔLEU2 pdr1ΔLEU2 pdr3ΔhisG::URA3::hisG ade2 ade3 leu2 ura3 cyh2 |
| SPY50636 | rad52 | MATa rad52ΔURA3 erg6ΔLEU2 pdr1ΔLEU2 pdr3ΔhisG::URA3::hisG ade2 ade3 leu2 trp1 ura3 cyh2 |
| SPY50876 | rad50 top1 | MATa top1ΔURA3 rad50Δkan$^r$ erg6ΔTRP1 pdr1LEU2 pdr3hisG ade2 ade3-130 leu2 trp1 ura3 cyh2 |
| SPY50868 | TOP2 o/e | MATα URA3-GPDp-TOP2 erg6TRP1 pdr1LEU2 pdr3hisG ade2 ade3 leu2 trp1 ura3 cyh2 |
| SPY50939 | hdf1 | MATa hdf1Δ URA3 erg6ΔTRP1 pdr1ΔLEU2 pdr3ΔhisG ade2 ade3 leu2 ura3 cyh2 |
| BY4705 | Wild type | MATα ade2hisG his3200 leu2 lys2 met15 trp163 ura3 |

Toxicity Assays in Yeast

Yeast toxicity assays were performed essentially as follows: Exponentially growing cultures of the appropriate strains were diluted in synthetic complete media to a concentration of $7.4 \times 10^4$ cells/mL, and aliquots (135 μL) were transferred to each well of clear flat-bottomed 96 well plates. Compounds were added in duplicate or triplicate as 15 μL of the appropriate dilution in 5% DMSO. A 15 μL portion of 5% DMSO was added to control wells. Assay plates were incubated at 30° C. for approximately seven generations growth in solvent control wells (as monitored by $OD_{660}$, typically 21–24 hours), then the $OD_{660}$ of the cultures was measured in a microplate reader (Bio-Tek). Cell growth ($OD_{660}$) in treated wells was plotted as a percentage of the growth in at least four averaged solvent control wells for the same strain. Camptothecin sodium salt (camptothecin Na) was the agent used in all yeast assays as standard.

Mammalian and Vertebrate Cell Culture.

Cell lines were grown at 37° C. in an atmosphere of 5% $CO_2$. The chicken pre-B cell line DT40 and its derivatives (Bezzubova, et al., *Cell* 89: 185–93 (1997), Takata, et al., *EMBO Journal* 17: 5497–508 (1998), Yamaguchi-Iwai, et al., *Molecular & Cellular Biology* 18: 6430–5 (1998)) were grown in RPMI containing 10% fetal calf serum and 1% chicken serum. The remaining cell lines were grown in DMEM with 10% fetal calf serum.

Toxicity Assays in Mammalian and Vertebrate Cells.

Toxicity assays in mammalian cell lines were performed using tritiated thymidine incorporation as a measure of the number of viable cells. In control experiments this method was found to have excellent agreement with colony forming assays using the same compounds on the same cell lines. Drug toxicity was measured as follows:

Cells were plated at a density of 500 cells per well in opaque 96 well plates (Packard) in a volume of 135 μL per well of the appropriate media. The plates were incubated overnight to allow cell adherence. Seven two-fold dilutions of the test compounds were added in a volume of 15 μL per well in triplicate, and 15 μL of media containing an appropriate concentration of DMSO was added to control wells in triplicate. Plates were incubated at 37° C. for 96 hours. The media was then replaced with 100 μL per well of the appropriate media containing 2 μCi/mL of (methyl-$^3$H) thymidine (Amersham Pharmacia Biotech), then plates were incubated for a further 24 hours at 37° C. Cells were washed three times with PBS, then 100 μL per well of scintillant was added (Microscint 20, Packard), and sealed plates were counted in a microplate reader (Packard Topcount). For suspension chicken cells, (methyl-$^3$H) thymidine was added directly to the drug-containing media at a concentration of 20 μCi/mL (comprising one tenth of the media volume) and incubated overnight. The suspension cells were transferred to a UniFilter GF/C plate (Packard) and washed with PBS in a plate washer (Packard). After drying, 25 μL per well of scintillant (Microscint 20, Packard) was added, and sealed plates were counted. Toxicity is expressed as a percentage of the control counts. For experiments involving shorter exposures to compounds, cells were grown in the presence of compound for the appropriate time, then the media was replaced with fresh drug-free media, and incubation continued for the remainder of 96 hours, followed by the normal tritiated thymidine uptake and washing protocol.

Compounds

Camptothecin, etoposide and hydroxyurea were obtained from Sigma. Topotecan, idarubicin, camptothecin Na, compound Ia and compound IIa were provided by the Developmental Therapeutics Program of the National Cancer Institute. All compounds were prepared in 100% DMSO, and diluted to 5% DMSO just before use.

Screen for rad50/52-Specific Compounds in Yeast.

Figure 3:
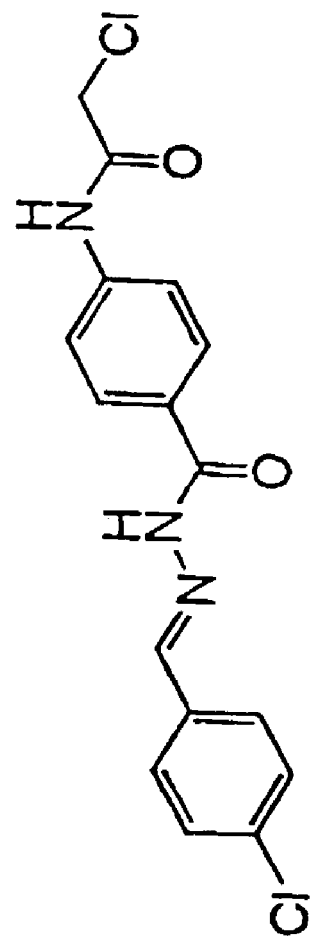
FIG. 3 illustrates the chemical structures of compound Ia and compound IIa.
Figure 3:
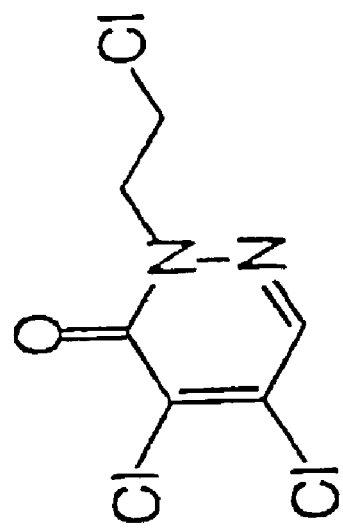

Compounds that induce double strand breaks without inducing other toxic lesions in DNA were identified by screening against DSB repair defective rad50 and rad52 strains of *Saccharomyces cerevisiae*, further showing that the compounds were not toxic in nucleotide excision repair defective (rad14) or daughter strand gap repair defective (rad18) strains (see FIG. 1). Agents with this profile include the Topo I and II poisons camptothecin Na, mitoxantrone and idarubicin. Additionally, this profile of activity excludes alkylating and cross-linking agents such as cis-platin, mitomycin C, thiotepa, lomustine and streptozocin, and antimetabolites such as hydroxyurea. As seen in FIG. 3, compounds Ia and IIa also fit the profile for selective toxicity and are unrelated to known topoisomerase poisons.

Compounds Ia and IIa are Novel Topo I Poisons.

Since the majority of the rad50/52 specific compounds appear to be Topo poisons, compounds I and II were tested to determine if they target topoisomerases using yeast strains that have altered expression levels of either Topo I or Topo II (Nitiss, et al., *Annals of the New York Academy of Sciences* 803: 32–43 (1996), Reid, et al., *Biochimica et Biophysica Acta*. 1400: 289–300 (1998)). For Topo I, a strain was constructed to carry a deletion of the TOP1 gene (top1). As neither compounds Ia or IIa produce toxicity in wild-type strains at the highest concentration used, the TOP1 deletion was constructed in the more sensitive rad50 background. Since Topo II is essential (Holm, et al. Cell 41: 553–63 (1985), Holm, et al., *Molecular & Cellular Biology* 9: 159–68 (1989)), a strain that overexpressed the TOP2 gene (TOP2oe) was used. Overexpression of TOP2 was found to be synthetically lethal with rad50, therefore the TOP2oe strain was constructed in the wild-type RAD50 background.

Figure 2A:
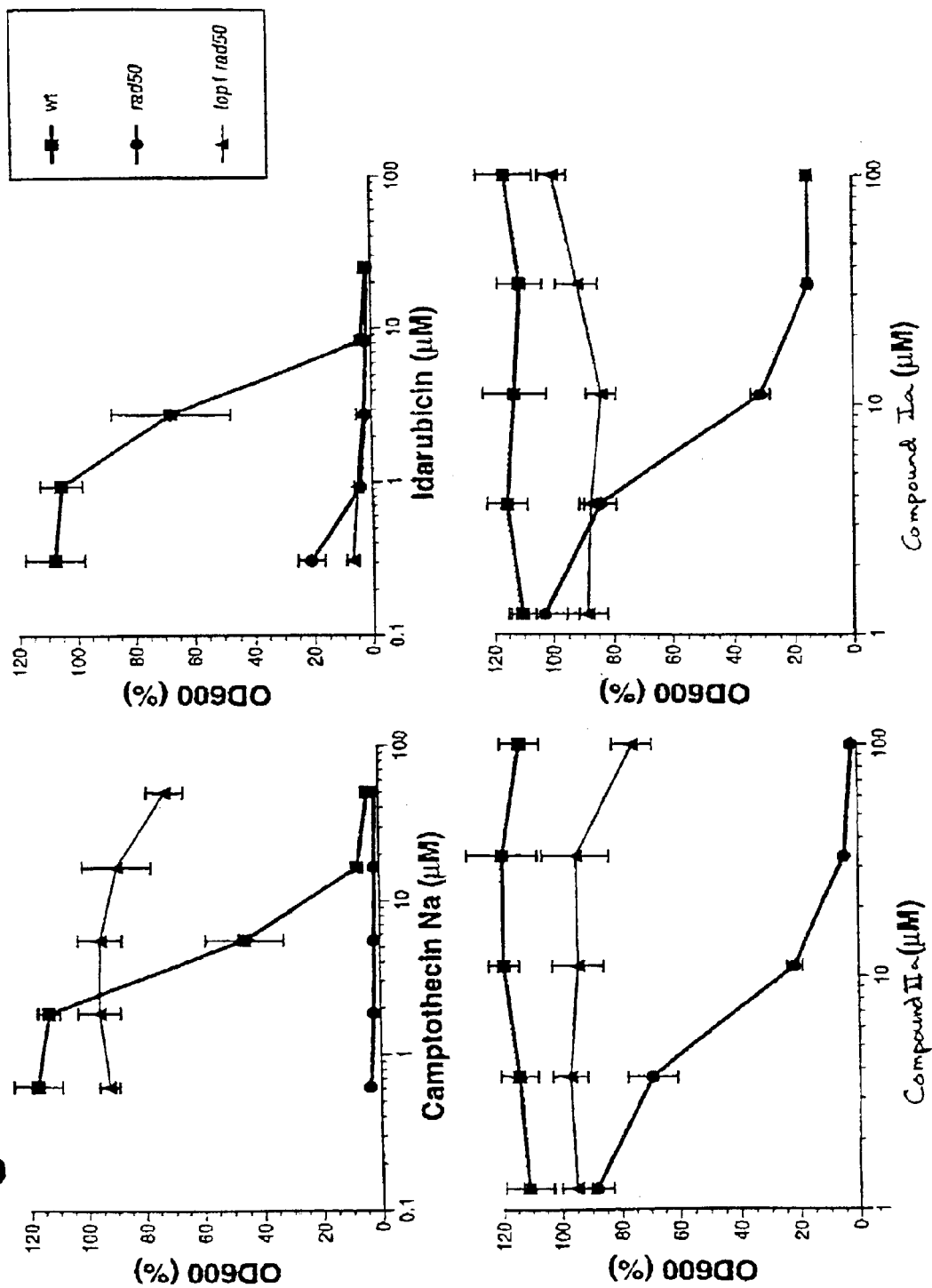
FIG. 2A shows the effects of camptothecin Na, idarubicin, compound Ia and compound IIa on yeast strains that are DSB repair defective, with (rad50) or without Topo I (rad50, top1), and a wild type control (wt).
Figure 2B:
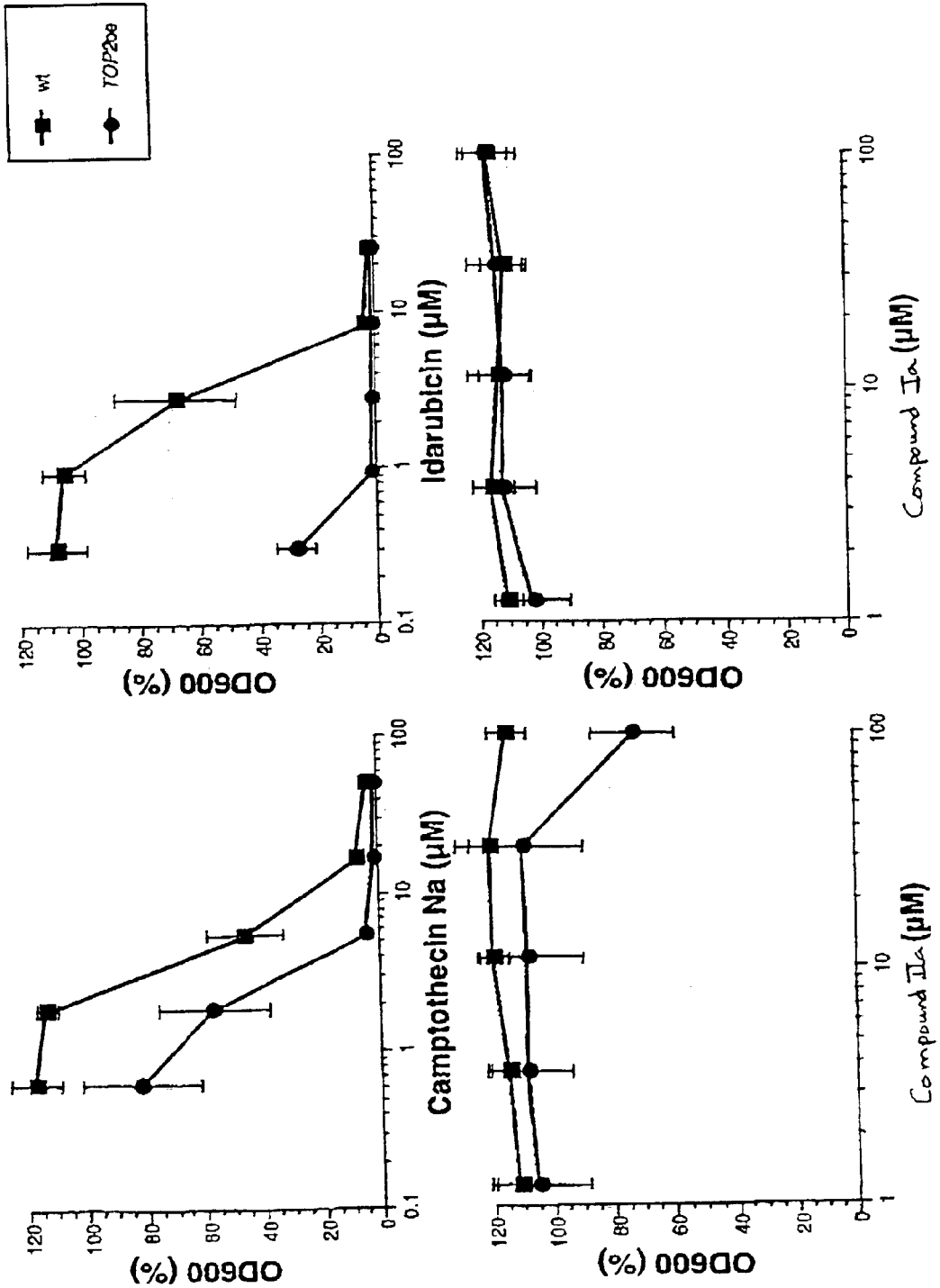
FIG. 2B shows the effects of altered levels of Topo II. Strains are wild-type (wt) or constitutively overexpressing Topo II (TOP2oe).

Sensitivity to camptothecin Na (Topo I poison), idarubicin (Topo II poison), compound Ia and compound IIa was measured in strains with altered Topo I levels (FIG. 2A) or Topo II levels (FIG. 2B). As expected deletion of the TOP1 gene greatly reduces the toxicity of camptothecin Na and has little effect on idarubicin toxicity (FIG. 2A). Overexpression of Topo II causes a slight increase in camptothecin Na toxicity and a large increase in idarubicin toxicity (FIG. 2B). The toxicity of both compound Ia and IIa is greatly reduced in strains carrying a deletion of the TOP1 gene (FIG. 2A), demonstrating that these compounds are Topo I poisons. Neither compound shows a large increase in toxicity when Topo II is overexpressed (FIG. 2B). Thus, the toxicity produced by either compound in yeast appears to be entirely attributable to its action as a Topo I poison (FIG. 2A). We attempted to confirm this finding with an in vitro assay for DNA strand-break formation in the presence of purified Topo I. Under conditions where camptothecin does induce strand-break formation, we did not detect strand-break induction by compounds Ia or IIa (data not shown). However, the relatively low sensitivity of this in vitro assay (requiring a camptothecin concentration 100-fold higher than cell-based assays), coupled with the higher IC50's of compounds Ia and IIa compared to camptothecin in cell based assays may have provided a negative result.

Repair of Compound Ia and IIa-Mediated Damage by Homologous Versus Non-Homologous DSB Repair Eukaryotic cells have two pathways for the repair of DSB's—homologous recombination and non-homologous end rejoining (NHEJ, Kanaar, et al, *Trends in Cell Biology,* 8: 483–9 (1998), Jeggo, et al., *Radiation Research* 150: S80–91 (1998)). The proteins Rad50, Rad52 and Rad54, amongst others, are required for homologous recombination and Ku70 and Ku80 are required for NHEJ (Kanaar, et al, *Trends in Cell Biology,* 8: 483–9 (1998), Jeggo, et al., *Radiation Research* 150: S80–91 (1998)). Homologous recombination is thought to be the most prevalent pathway for DSB repair in yeast, whereas in mammalian cells NHEJ is more important (Kanaar, et al, *Trends in Cell Biology,* 8: 483–9 (1998), Jeggo et al., *Radiation Research* 150: S80–91 (1998)).

Figure 4A:
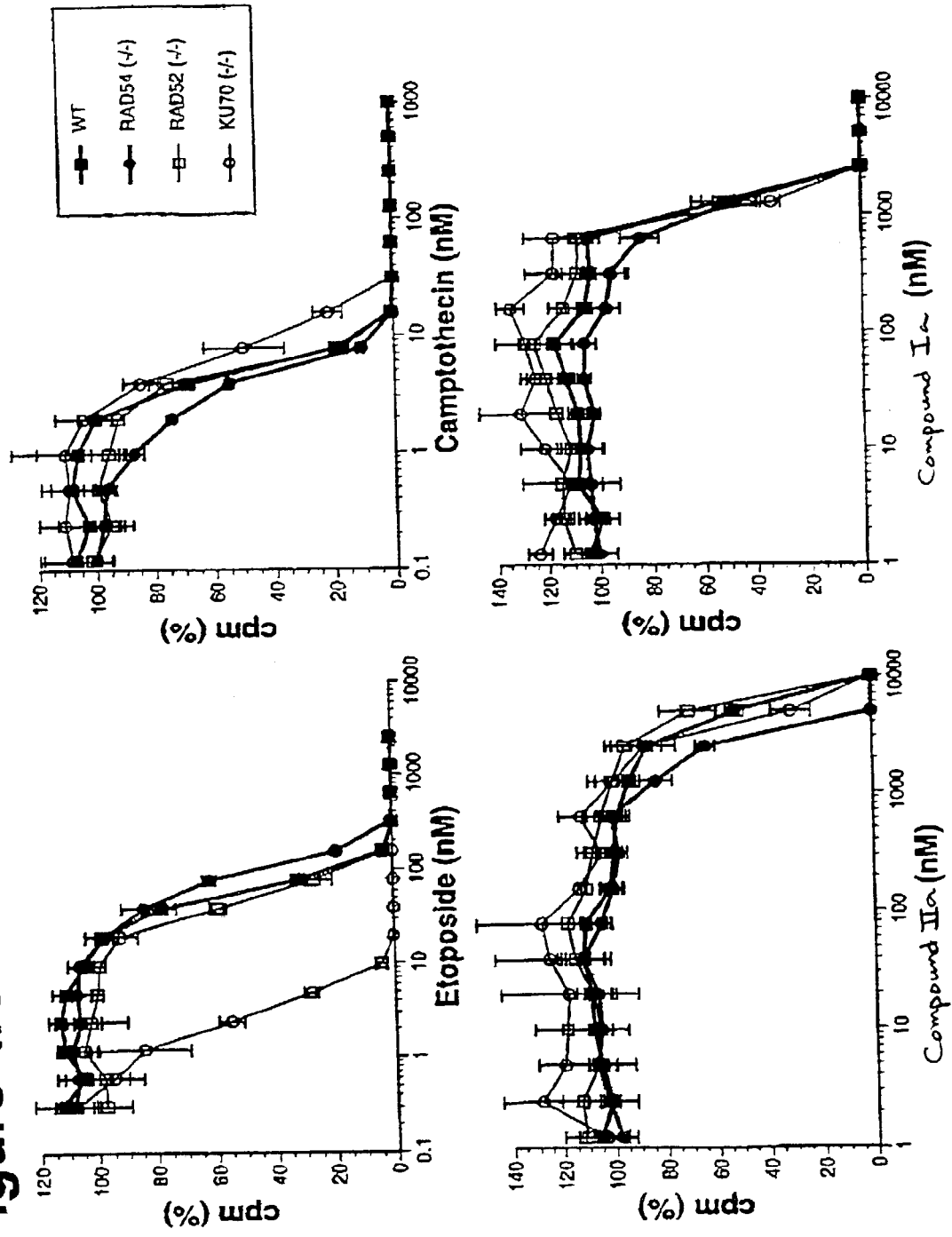
FIG. 4A shows the effect of homologous recombination and non-homologous end rejoining pathways of DSB repair on toxicity. The toxicity of camptothecin (Topo I poison), etoposide (a Topo II poison), compound Ia and compound IIa was measured in an isogenic set of cell lines derived from the chicken pre-B cell line DT40 with or without expression of the DSB repair proteins RAD52. RAD54 (both homologous recombination) and KU70 (non-homologous end rejoining).

Both Topo I and Topo II poisons are selectively toxic in yeast cells lacking RAD50 or RAD52, indicating that homologous recombination is required to repair the toxic lesions induced by these compounds. The sensitivity of yeast lacking Ku70 (encoded by the HDF1 gene) to camptothecin Na, compounds Ia and IIa, has now been examined. These studies indicated that sensitivity in this NHEJ-deficient mutant is indistinguishable from that of wild-type for all three agents. Thus the NHEJ pathway is not important for the repair of lesions induced by these compounds in yeast. In the mammailian system, Topo II but not Topo I poisons selectively kill cells lacking KU80 expression (S. Goehle, C. Ludlow and J. Lamb, unpublished results; and Caldecott, et al., *Mutation Research* 255: 111–21 (1991)). In the case of Topo II poisons, the drug/enzyme complex directly produces a DSB, which could occur in all phases of the cell cycle and can apparently be repaired by either DSB repair pathway. Topo I poisons, however, create a single strand break that is converted to a DSB by passage of a replication fork during ongoing DNA synthesis (D'Arpa, et al., *Cancer Research* 50: 6919–24 (1990), Hsiang, et al., *Cancer Research* 49: 5077–82 (1989), Holm, et al., *Cancer Research* 49: 6365–8 (1989)). It has been proposed that DSB's created in this context can only be repaired by homologous recombination, additionally requiring proteins involved in sister chromatid cohesion (Castano, et al., *Genes & Development* 10: 2564–76 (1996), Castano, et al., *Nucleic Acids Research* 24: 2404–10 (1996), Walowsky, et al., *Journal of Biological Chemistry* 274: 7302–8 (1999)). The toxicity of a Topo I poison (camptothecin), a Topo II poison (etoposide), compound Ia and compound IIa were compared in an isogenic set of cells derived from the chicken pre-B cell line DT40 (Bezzubova, et al., *Cell* 89: 185–93 (1997), Takata, et al., *EMBO Journal* 17: 5497–508 (1998), Yamaguchi-Iwai et al., *Molecular & Cellular Biology* 18: 6430–5 (1998)) with and without expression of either the NHEJ DSB repair protein KU70, or the homologous recombination repair proteins RAD52 or RAD54 (see FIG. 4A). As expected, etoposide is selectively toxic in cells lacking KU70, whereas camptothecin toxicity is unaffected by KU70 expression. Loss of homologous recombination (lack of RAD52 or RAD54) has no effect on the toxicity of etoposide and a minor effect on the toxicity of camptothecin. Apparently homologous recombination is not a significant pathway of DSB repair in this system, probably because of its much reduced levels in higher eukaryotes. This suggests that vertebrate cells, compared to yeast cells, have a greatly reduced ability to repair the DSB's induced by Topo I poisons (see FIG. 4A). Like camptothecin and unlike etoposide, compound Ia and compound IIa toxicities are unaffected by loss of KU70 and only marginally affected by loss of RAD52 or RAD54 (see FIG. 4A). Therefore these two classes of compounds, like other Topo I poisons, induce damage in vertebrate cells that cannot be repaired by the NHEJ pathway of DSB repair and is repaired only to a minor extent by homologous recombination.

Compound Ia and Compound IIa are Active in Tumor Cell Lines that Overexpress MDR1

Figure 4B:
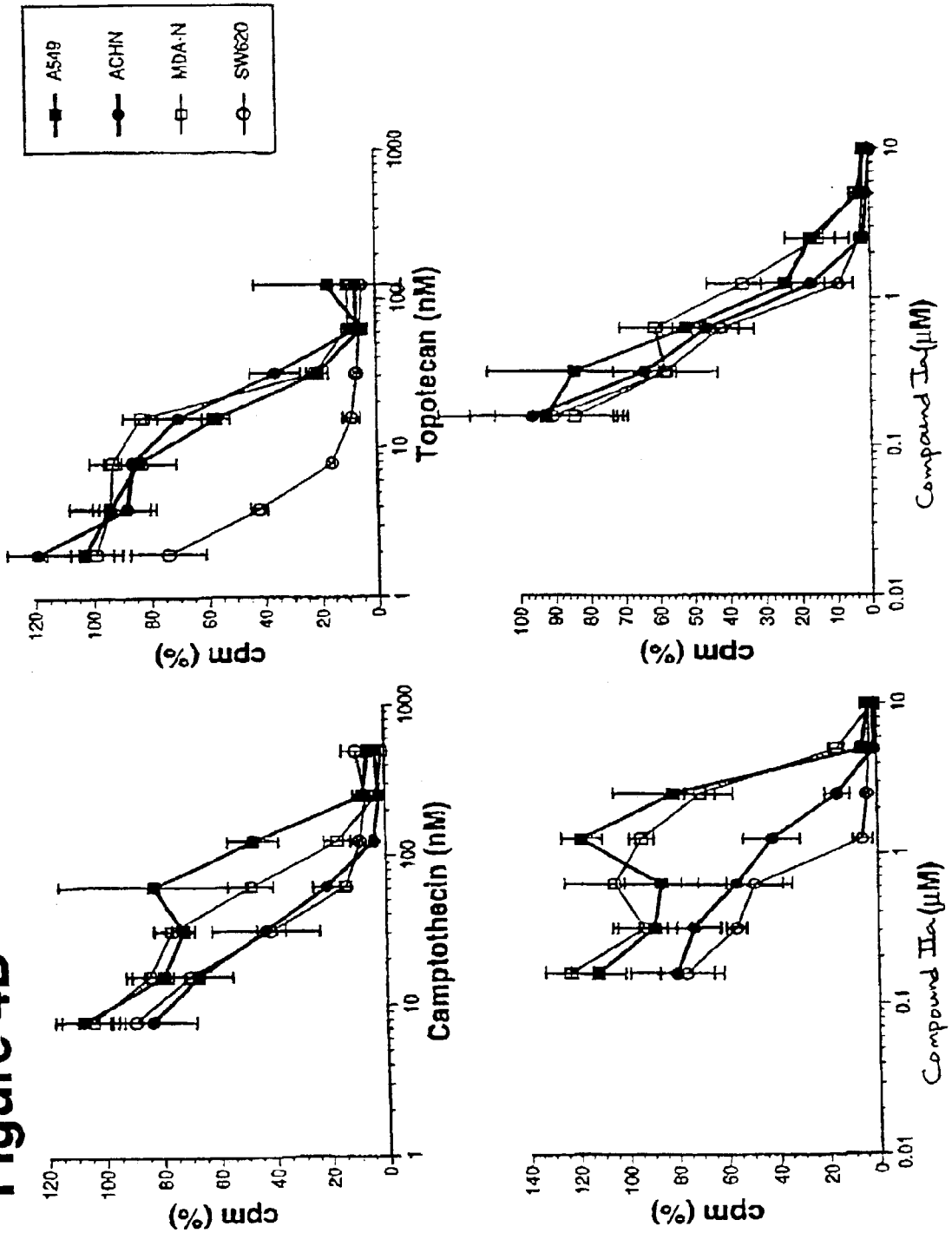
FIG. 4B shows the toxicity of the Topo I poisons camptothecin, topotecan, compound Ia and compound IIa were measured in four cancer derived cell lines. The MDR1 activities for these cell lines are as follows—ACHN-120. SW620—31. A549—10. MDA-N— unknown.

A common mechanism of tumor resistance to chemotherapeutic agents is overexpression of the drug efflux protein MDR1 (Kane, et al., *Advances in Drug Research* 28: 182–252 (1996), Nooter, et al., *Leukemia Research* 18: 233–43 (1994)). MDR1 is overexpressed in many tumor derived cell lines (for instance see http://dtp.nci.nih.gov/), and its overexpression inversely correlates with sensitivity to certain compounds (Kane, et al., *Advances in Drug Research* 28: 182–252 (1996)). Four tumor derived cell lines representing a variety of tumor types were selected (in three of which the level of expression of MDR1 has been determined by rhodamine efflux: A549, 10; SW620, 31; ACHN, 120; see http://dtp.nci.nih.gov/), and their sensitivity to camptothecin, topotecan, compound Ia and compound IIa was tested (FIG. 4B). Sensitivity to the MDR1 substrate taxol shows a clear inverse correlation with MDR1 levels in these cells. No correlation was observed between the level of MDR1 activity and the toxicity of the four compounds. For example, ACHN is more sensitive than A549 to compound IIa even though ACHN has greater than ten fold more MDR1 activity. This indicates that MDR1 activity is not a major determinant of the toxicity of these compounds in these cell lines. All four compounds are most effective against the colon carcinoma derived cell line SW620, although no significant differences in toxicity were observed with compound Ia (See FIG. 4B).

Figure 5:
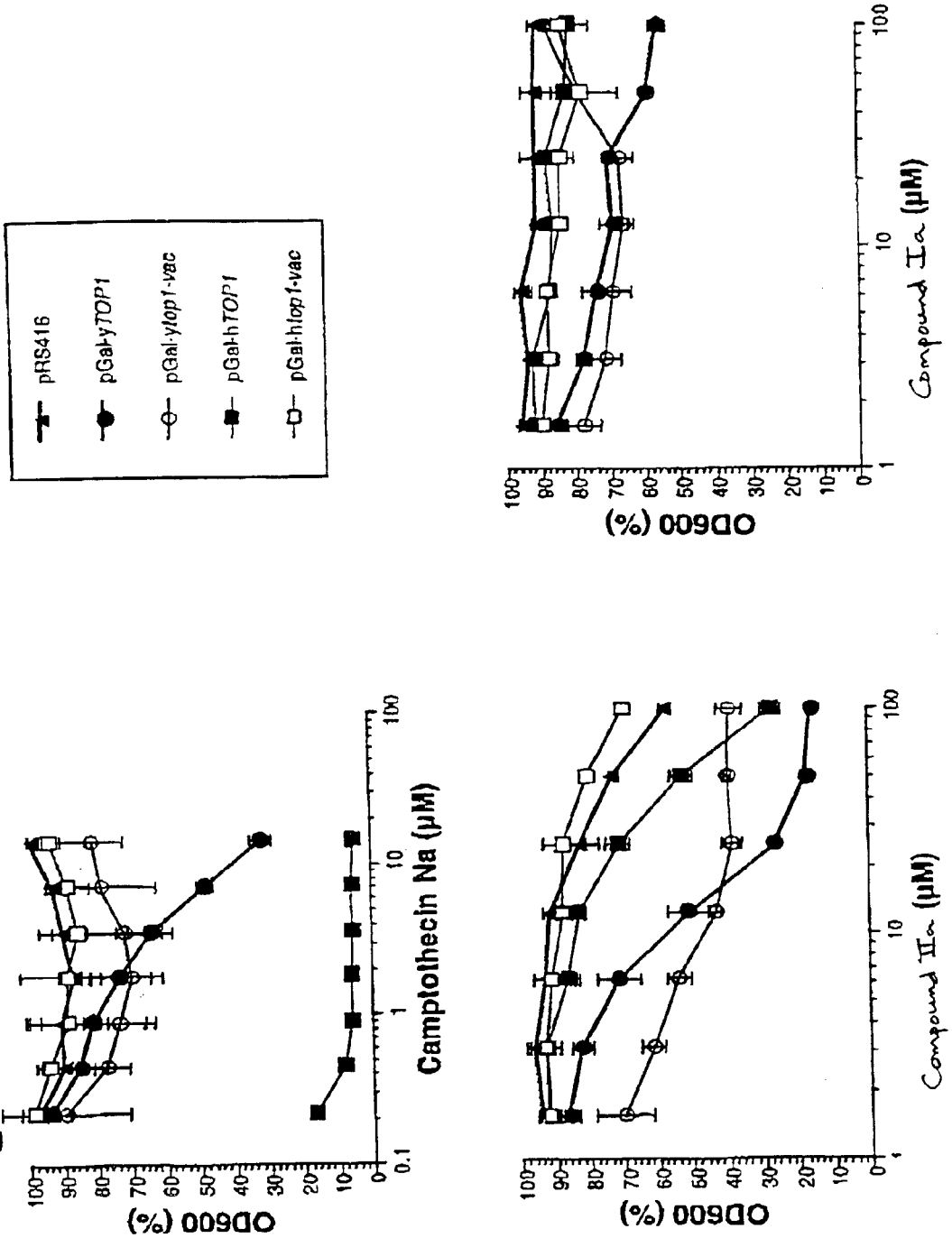
FIG. 5 illustrates the effect of overexpression of yeast and human (wild type or mutant) Topo I in yeast. The toxicity of camptothecin Na, compound Ia and compound IIa were measured in wild-type strains containing plasmids that direct the overexpression of yeast (pyTOP1) and human (phTOP1) topo I or carnptothecin-resistant mutant versions of yeast (pytop1-vac) and human (phtop1-vac) Topo I, compared to vector (pRS416).

Activity of Compounds Ia and IIa with Human Topoisomerase I and Topo I-VAC Mutants The experiments described above demonstrate that compounds Ia and IIa are Topo I poisons in yeast (FIGS. 1 & 2) and are toxic in human cancer and vertebrate cells (FIG. 4). These compounds were also examined for their ability to target human Topo I directly. In this regard, the sensitivity of yeast strains overexpressing either human or yeast topoisomerase I genes (hTOP1 or yTOP1, respectively) under the control of the inducible GAL promoter (see, for example, Knab, et al., *Journal of Biological Chemistry* 268: 22322–30 (1993); and Knab, et al., *Journal of Biological Chemistry* 270: 6141–8 (1995)) were used. Additionally, the sensitivity of yeast overexpressing the Topo I-VAC mutant enzyme, containing two amino acid substitutions (htop1-vac and ytop1-vac) that render topoisomerase I insensitive to the action of camptothecin were also examined (see, for example, Knab, et al., *Journal of Biological Chemistry* 268: 22322–30 (1993); and Knab, et al., *Journal of Biological Chemistry* 270: 6141–8 (1995)). Briefly, yeast strains (wild-type at both TOP1 and RAD50 loci) harboring plasmid-borne pGal-TOP1 genes were grown in the presence of galactose to induce Topo I expression, then grown in the presence of camptothecin, compound Ia and compound IIa (see FIG. 5). As previously described (ibid.), overexpression of the yeast or human TOP1 genes, but not the equivalent VAC mutants, accentuates the toxicity of camptothecin Na (see FIG. 5). Similarly, overexpression of the yeast and human TOP1 genes accentuates the toxicity of at least compound IIa (FIG. 5), indicating that compound IIa is capable of targeting human Topo I. In contrast to camptothecin Na, however, compound IIa is effective with both yTOP1 and ytop1-vac (FIG. 5). The yTOP1-vac gene produces a dominant slow-growth phenotype that creates difficulty in assessing drug sensitivity using a standard assay monitored by relative OD660. Accordingly, the yTOP1vac results shown in FIG. 5 were confirmed by monitoring cell survival by colony formation after treatment. These experiments confirmed that the toxicity of compound IIa, but not camptothecin, is accentuated in yeast overexpressing yTOP1-vac compared to the vector control. Together these data show that compound IIa and camptothecin interact with Topo I in distinct manners.

Little or no accentuation of the toxicity of compound Ia is seen in the yTOP1 or hTOP1 overexpressing strains. This may be because compound Ia cannot induce sufficient toxicity in these DSB repair-proficient and yeast strains. In addition, we find that yeast sensitivity to compound Ia, unlike compound IIa, is strongly influenced by the sensitizing mutations erg6 pdr1 and pdr3 present in the screening strains that identified these compounds.

Effects of Length of Exposure and DNA Synthesis Inhibition.

Camptothecin toxicity is strongly dependent upon the length of exposure and can be inhibited by DNA synthesis inhibitors (D'Arpa, et al., *Cancer Research* 50: 6919–24 (1990), Hsiang, et al., *Cancer Research* 49: 5077–82 (1989), Holm, et al., *Cancer Research* 49: 6365–8 (1989)). Effects of exposure time and co-treatment with the DNA synthesis inhibitor hydroxyurea (HU) were examined for the toxicity induced by compounds Ia and IIa. Rat1a fibroblasts were exposed to topotecan, etoposide, compound Ia or compound IIa for either four or six hours (FIG. 6A). As expected, the Topo I poison topotecan shows a strong time dependency with a six-hour exposure being much more effective than a four-hour exposure. By contrast, there is little difference in toxicity between four and six hour exposures to the Topo II poison etoposide (FIG. 6A), presumably because Topo II mediated DSB formation can occur in all phases of the cell cycle (Larsen, et al., *Biochimica et Biophysica Acta.* 1400: 257–74 (1998). Wilson, et al., *Radiation Research* 87: 121–36 (1981), Sullivan, et al., *Biochemistry* 25: 2248–56 (1986)). Unexpectedly, four hour versus six hour exposures are also equally effective for both compound Ia and IIa (FIG. 6A). In additional experiments etoposide, compound Ia and compound IIa demonstrated nearly full toxicity with a two hour exposure, whereas camptothecin shows no toxicity at two hours. Furthermore, camptothecin is as much as 100 fold more effective with a 96 hour exposure as with a four hour exposure, whereas the same exposure difference produces only a three- to five-fold effect for compounds Ia and IIa. These results indicate that although these compounds, like camptothecin, require Topo I for toxicity, the production of toxic lesions by these compounds is not restricted to S-phase.

A six-hour exposure was used to test whether the toxicity of the same set of compounds is dependent on ongoing DNA synthesis. Rat1a fibroblasts were exposed to topotecan, etoposide, compound Ia and compound IIa in combination with either 0, 0.25, 0.5 or 1 mM HU (FIG. 6B). As previously reported, HU suppresses the toxicity of the Topo I poison topotecan but not the Topo II poison etoposide (D'Arpa, et al., *Cancer Research* 50: 6919–24 (1990), Hsiang, et al., *Cancer Research* 49: 5077–82 (1989), Holm, et al., *Cancer Research* 49: 6365–8 (1989)). Unlike topotecan, the Topo I poisons compounds Ia and IIa are not inhibited by co-treatment with HU (FIG. 6B); rather, co-treatment causes a slight accentuation of toxicity. Thus, in contrast to camptothecin and topotecan, compounds Ia and IIa show no marked time dependency for toxicity (FIG. 6A) and are not inhibited by HU (FIG. 6B), indicating critical mechanistic differences between these compounds and camptothecin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for the treatment of a proliferative disorder selected from the group consisting of colorectal carcinoma, ovarian cancer, small cell lung cancer and non-Hodgkin's lymphoma, said method comprising administering to a subject in need of such treatment an effective amount of a compound of formula I,

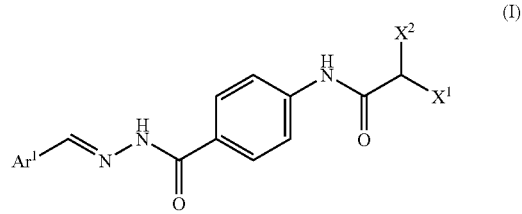

wherein $X^1$ is H or Cl and $X^2$ is F or Cl; and $Ar^1$ is a member selected from the group consisting of substituted or unsubstituted aryl.

2. A method in accordance with claim 1, wherein $X^1$ is H, $X^2$ is Cl, and $Ar^1$ is selected from the group consisting of 4-chlorophenyl and 4-nitrophenyl.

3. A method for selectively inducing DNA double strand breaks in a cell in all phases of the cell cycle without inhibiting nucleotide excision repair or daughter strand gap repair in said cell, said method comprising contacting said cell with a compound of formula I,

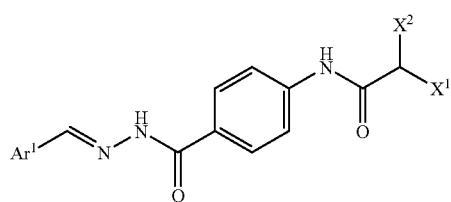
(I)

wherein $X^1$ is H or Cl and $X^2$ is F or Cl; and $Ar^1$ is a member selected from the group consisting of substituted or unsubstituted aryl; and thereby treating a proliferative disorder selected from the group consisting of colorectal carcinoma, ovarian cancer, small cell lung cancer and non-Hodgkin's lymphoma.

4. A compound of formula I,

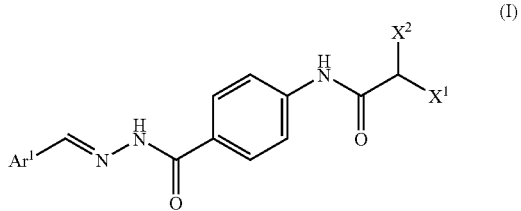
(I)

wherein $X^1$ is H or Cl and $X^2$ is F or Cl; and $Ar^1$ is a member selected from the group consisting of substituted or unsubstituted aryl.

5. A pharmaceutical composition comprising a pharmaceutically acceptable excipient and a compound of formula I,

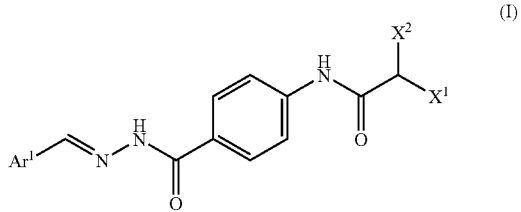
(I)

wherein $X^1$ is H or Cl and $X^2$ is F or Cl; and $Ar^1$ is a member selected from the group consisting of substituted or unsubstituted aryl.

* * * * *

UNITED STATES PATENT AND TRADEMARK OFFICE
CERTIFICATE OF CORRECTION

PATENT NO. : 7,173,063 B1 Page 1 of 1
APPLICATION NO. : 10/129936
DATED : February 6, 2007
INVENTOR(S) : John R. Lamb et al.

It is certified that error appears in the above-identified patent and that said Letters Patent is hereby corrected as shown below:

In the Specification:

Column 1, line 11, replace "(N01BC65017)" with --(N01BCM065017)--

Signed and Sealed this

Eleventh Day of November, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,173,063 B1 | |
| APPLICATION NO. | : 10/129936 | |
| DATED | : February 6, 2007 | |
| INVENTOR(S) | : John R. Lamb et al. | |

It is certified that error appears in the above-identified patent and that said Letters Patent is hereby corrected as shown below:

In the Specification:

Column 1, line 11, replace "(N01BC65017)" with --(CM065017)--

This certificate supersedes the Certificate of Correction issued November 11, 2008.

Signed and Sealed this

Seventh Day of July, 2009

JOHN DOLL
*Acting Director of the United States Patent and Trademark Office*